United States Patent
Hunke et al.

(10) Patent No.: US 8,920,605 B2
(45) Date of Patent: *Dec. 30, 2014

(54) FLUORESCENT WHITENING AGENT COMPOSITIONS

(75) Inventors: Bernhard Hunke, Hennef (DE); Andrei Tauber, Cologne (DE); Michael Kraemer, Kurten (DE); Günter Klug, Langenfeld (DE)

(73) Assignee: Blankophor GmbH & Co. KG (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/006,860

(22) PCT Filed: Mar. 22, 2012

(86) PCT No.: PCT/EP2012/001264
§ 371 (c)(1),
(2), (4) Date: Oct. 21, 2013

(87) PCT Pub. No.: WO2012/126628
PCT Pub. Date: Sep. 27, 2012

(65) Prior Publication Data
US 2014/0034258 A1    Feb. 6, 2014

(30) Foreign Application Priority Data

Mar. 24, 2011  (EP) ..................... 11002479

(51) Int. Cl.
*D21F 11/00*  (2006.01)
(52) U.S. Cl.
USPC ........................................ 162/158

(58) Field of Classification Search
USPC ................. 162/158; 8/648, 119; 252/301.23; 544/193.2
See application file for complete search history.

(56) References Cited

FOREIGN PATENT DOCUMENTS

| EP | 0884312 A1 | 12/1998 |
|---|---|---|
| EP | 1752453 A1 | 2/2007 |
| EP | 2431519 A1 | 3/2012 |
| WO | 9842685 A1 | 10/1998 |
| WO | 0119804 A1 | 3/2001 |
| WO | 02055646 A1 | 7/2002 |
| WO | 2006045714 A1 | 5/2006 |
| WO | 2012126628 A8 | 9/2012 |

OTHER PUBLICATIONS

International Preliminary Report on Patentability issued in International Application No. PCT/EP2012/001264, dated Sep. 24, 2013; 6 pages.
International Search Report issued in International Application No. PCT/EP2012/001264, mailed May 25, 2012; 5 pages.
Written Opinion of the International Searching Authority issued in International Application No. PCT/EP2012/001264, mailed May 25, 2012; 5 pages.

*Primary Examiner* — Mark Halpern
(74) *Attorney, Agent, or Firm* — Cantor Colburn LLP

(57) ABSTRACT

The invention relates to a composition suitable for optically whitening paper or board, wherein the composition contains specified bis-triazinylamino-stilbene fluorescent whitening agents with carboxylic acid and/or sulfonic acid groups. The composition can be used for whitening paper in the pulp, size press or by coating.

12 Claims, No Drawings

FLUORESCENT WHITENING AGENT COMPOSITIONS

This application is a 371 of PCT/EP2012/001264 filed 22 Mar. 2012.

BACKGROUND

The present invention relates to fluorescent whitening agent compositions containing specific bis-triazinylamino-stilbene fluorescent whitening agents with carboxylic acid and/or sulfonic acid groups for whitening paper or board.

It is well known that the whiteness of paper and board can be improved by the addition of fluorescent whitening agents (FWAs). The most important fluorescent whitening agents used in the paper and board industry are anilino-substituted bistriazinyl derivatives of 4,4'-diaminostilbene-2,2'-disulfonic acid (flavonic acid). From these fluorescent whitening agents disulfo-, tetrasulfo- and hexasulfo-types are known. The disulfo-type fluorescent whitening agents with no sulfonic acid groups at the aniline rings have a low solubility in water and a high affinity for cellulose fibres. They are especially suitable for use at the wet-end of paper making process. The hexasulfo-type fluorescent whitening agents with two sulfonic acid groups at each aniline ring have a high solubility in water and a low affinity for cellulose fibres. They are more specialty products when very high whiteness is desired. The tetrasulfo-type fluorescent whitening agents with one sulfonic acid group at each aniline ring exhibit a behaviour between the disulfo- and hexasulfo-type fluorescent whitening agents and are most commonly used for whitening paper or board.

For ease of handling and metering, the paper and board industry demands fluorescent whitening agents to be supplied in a liquid form, preferably as a concentrated aqueous solution, which should be stable to prolonged storage over a wide temperature range. Due to the low solubility of disulfo-type fluorescent whitening agents in water, currently solubilising auxiliaries such as urea, triethanolamine or diethylene glycol are added in amounts of up to 30% to provide storage stability for concentrated aqueous solutions of disulfo-type fluorescent whitening agents. These solubilising agents have no affinity to cellulose and contaminate the effluent from the paper mill, thus being undesired. EP-A-1 752 453 teaches storage stable solutions of disulfo-type fluorescent whitening agents which contain specific counter-ions for the sulfonic acid groups, which counter-ions are derived from specific aminoalkanols. WO 02/055646 A1 discloses concentrated aqueous solutions containing a mixture of two specific disulfo-type fluorescent whitening agents. Alternatively, slurries or dispersions of disulfo-type fluorescent whitening agents in water are known, e.g. from EP 0 884 312 B1. However, in order to enable the metering of homogenous preparations into the papermaking process, usually stirring is required.

BRIEF SUMMARY

Surprisingly, it has been found that problems of the prior art can be overcome by using mixtures or combinations of specific bis-triazinylamino-stilbene fluorescent whitening agents having carboxylic acid and/or sulfonic acid groups at the terminal phenyl rings. These mixtures or combinations when used for whitening paper or board yield paper or board of improved whiteness. Further, the production process of those fluorescent whitening agents is more cost-effective, compared to that of the commonly used disulfo-type fluorescent whitening agents, since it dispenses with laborious isolation and filtration steps. Moreover, the disulfo-type fluorescent whitening agents thereof enable stable concentrated aqueous preparations or solutions to be formed, without addition of solubilising auxiliaries.

DETAILED DESCRIPTION

The present disclosure relates to fluorescent whitening agent (FWA) compositions suitable for optically whitening paper or board, wherein the composition contains at least two fluorescent whitening agents selected from the fluorescent whitening agents of the formula (1), formula (2) and formula (3)

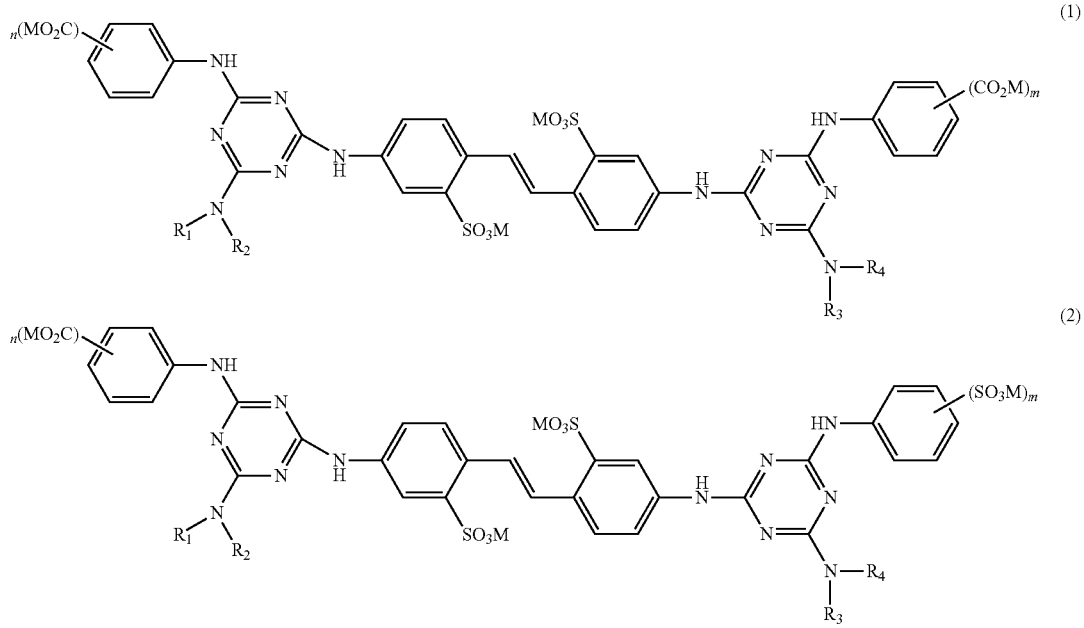

-continued

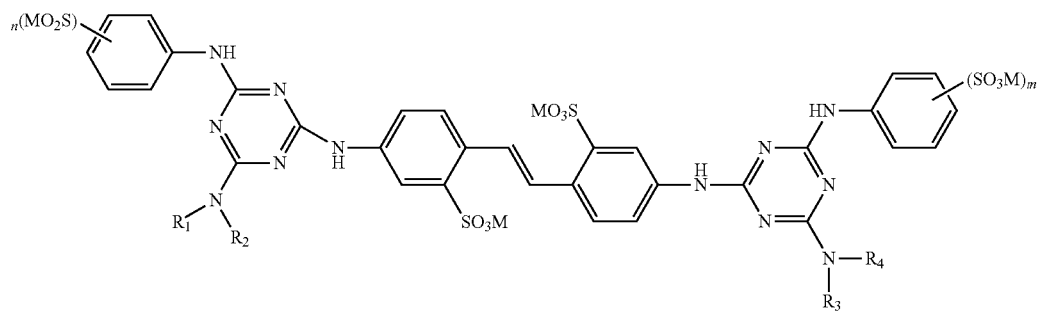

(3)

wherein n and m are, independently of each other, 0, 1, or 2, with the proviso that n and m are not both 0; $R_1$, $R_2$, $R_3$ and $R_4$ represent, independently of each other, hydrogen, cyano, $C_1$-$C_4$ alkyl, $C_2$-$C_4$ hydroxyalkyl, $C_2$-$C_4$ cyanoalkyl or $C_1$-$C_4$ alkoxyalkyl, or the residue of an amino acid from which a hydrogen atom has been abstracted from the amino group; or $R_1$ and $R_2$, or $R_3$ and $R_4$, independently of each other, together with N atom form morpholine, piperidine or pyrrolidine ring; or —$(CH_2)_l$—$SO_3M$, where l is 1, 2 or 3; or —$(CH_2)_i$—COOR, —$(CH_2)_i$—CONHR, —$(CH_2)_i$—COR, where i is an integer from 1 to 4, R is $C_1$-$C_3$ alkyl or has the same meaning as M; and M represents hydrogen, or one equivalent of a cation, in particular Li, Na, K, Ca, Mg, ammonium, or ammonium which is mono-, di-, tri- or tetra-substituted by $C_1$-$C_4$ alkyl or $C_2$-$C_4$ hydroxyalkyl.

The present disclosure also refers to the fluorescent whitening agent of formula (2) and the use of that fluorescent whitening agent and of the fluorescent whitening agent (FWA) compositions for optically whitening paper or board, e.g. in the pulp. Further, the disclosure relates to a process for optically whitening paper and to paper obtainable by that process. Preferred embodiments are described in the description hereinafter, and the claims In one embodiment, the fluorescent whitening agent composition is a wet-end composition, and the process is a process for whitening paper, wherein a pulp or pulp suspension is brought into contact with said composition. In another embodiment, the fluorescent whitening agent composition is used for preparing a size press liquor or a coating composition.

According to the disclosure, the composition or mixture contains at least two of the bis-triazinylamino-stilbene compounds of the above defined formulae (1), (2) and (3). In the context of the invention, in the formulae (1), (2) and (3) the alkyl group can be linear or branched, and the possible substituents of the alkyl group, which are alkoxy, cyano, and/or hydroxyl groups, can be attached at any position of the alkyl chain. In the present disclosure, $C_1$-$C_4$ alkoxyalkyl means $C_1$-$C_4$ alkyl substituted with $C_1$-$C_4$ alkoxy. In a preferred embodiment, $R_1$, $R_2$, $R_3$ and $R_4$ represent, independently of each other, $C_2$-$C_4$ hydroxyalkyl, $C_1$-$C_4$ alkoxyalkyl, or $C_1$-$C_4$ alkyl, preferably $C_2$-$C_4$ hydroxyalkyl or $C_1$-$C_4$ alkoxyalkyl, in particular hydroxyethyl or hydroxyisopropyl. In some embodiments, $R_1$, $R_2$, $R_3$ and $R_4$ represent hydroxyethyl.

In one embodiment, n and m are, independently of each other, 1 or 2. In other embodiments, n and m are both 1. Alternatively, in still other embodiments, n is 1 and m is 2, or n is 2 and m is 1. The groups —$SO_3M$ and —$CO_2M$ can be at any position of the terminal phenyl rings. Exemplary compounds in the composition are those where the groups —$SO_3M$ and —$CO_2M$ are, independently of each other, in ortho- or para-position, preferably in para-position. If n and/or m is/are 2, the group —$SO_3M$ and/or the group —$CO_2M$ can be in ortho- and para-position. An exemplary compound is a compound of formula (2), wherein n and m are both 1, the group —$SO_3M$ is in meta- or ortho-position, and the group —$CO_2M$ is in para-position. Another exemplary compound is a compound of formula (2), wherein n and m are both 1, the group —$SO_3M$ is in para-position, and the group —$CO_2M$ is in ortho-position.

Exemplary embodiments of M are hydrogen, Na, K, Ca, Mg, in other embodiments, M is Na, K or hydrogen, and in still other embodiments M is Na. The fluorescent whitening agents are used as free acids or as salts thereof, e.g., alkali metal salts.

The fluorescent whitening agents of formulae (1), (2) and (3) and the mixtures thereof can be prepared by known procedures. Generally, the compounds are prepared by reacting cyanuric chloride with 4,4'-diaminostilbene-2,2'-disulfonic acid or a salt thereof, aminobenzoic acid and/or aminosulfonic acid and/or the corresponding aniline compound with two carboxy acid or sulfonic acid groups, and substituted aliphatic amines or heterocyclic compounds. The ratio of aminobenzoic acid, aminosulfonic acid and/or aniline compound with two carboxy acid or sulfonic acid groups can be selected such that a desired ratio of the fluorescent whitening agents of formulae (1), (2) and/or (3) is obtained. PL patent 61710 discloses the preparation of some specific fluorescent whitening agents with one carboxylic acid group in p-position of each aniline ring without sulfonic acid group. The purification of the fluorescent whitening agents of formulae (1), (2) and (3) is easier and thus more cost-effective than for commonly used disulfo-type fluorescent whitening agents, since isolation and formulation steps can be avoided. The purification could be carried out by, for example, membrane filtration.

The composition of the fluorescent whitening agents of formulae (1), (2) and/or (3) can be produced in form of a mixture with the desired ratio of the fluorescent whitening agents of formulae (1), (2) and/or (3). Alternatively, the composition can be produced by preparing separately the fluorescent whitening agents of formulae (1), (2) and/or (3) by the methods known in the art and as described above, and then blending or mixing together in the desired ratio after their preparation.

The composition contains at least two, e.g., two or three, fluorescent whitening agents selected from the fluorescent whitening agents of formulae (1), (2) and (3). In one embodiment, the composition comprises the fluorescent whitening agents of the formulae (1) and (2). In another embodiment, the composition comprises the fluorescent whitening agents of the formulae (2) and (3). In still another embodiment, the composition comprises the fluorescent whitening agents of the formulae (1) and (3). In yet another embodiment, the composition contains at least two fluorescent whitening agents selected from the fluorescent whitening agents of formulae (1), (2) and (3), and one of those fluorescent whitening agents is the compound of formula (2). In another embodiment, the composition comprises the fluorescent whitening agents of the formulae (1), (2) and (3). The composition can also contain one or more of each of a fluorescent whitening agent of the formulae (1), (2) and/or (3). In addition, the composition can contain one or more known bis-triazinylamino-stilbene or distyryl-biphenyl based fluorescent whitening agents.

Exemplary compositions are shown below in the Embodiments 1 and 2, wherein M is as described above.

Embodiment 1

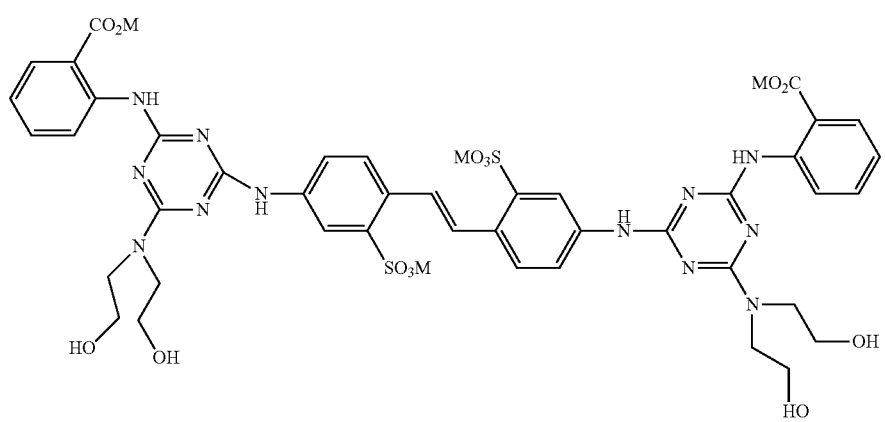

(1)

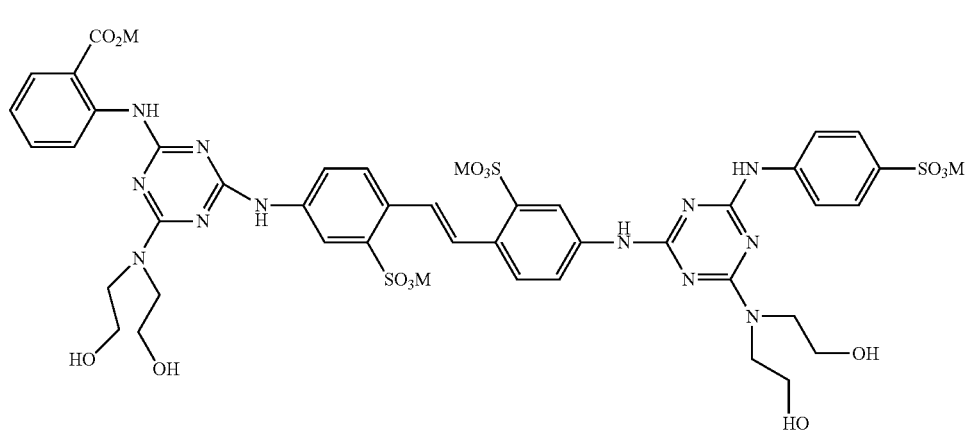

(2)

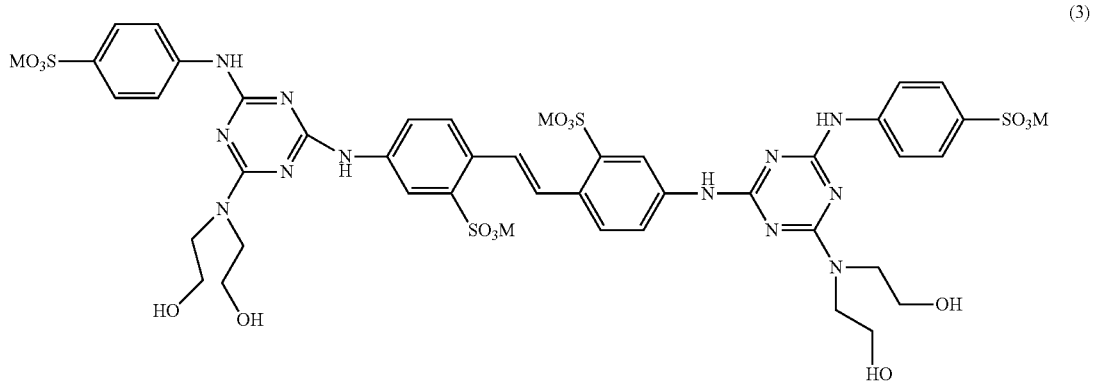

(3)

Embodiment 2

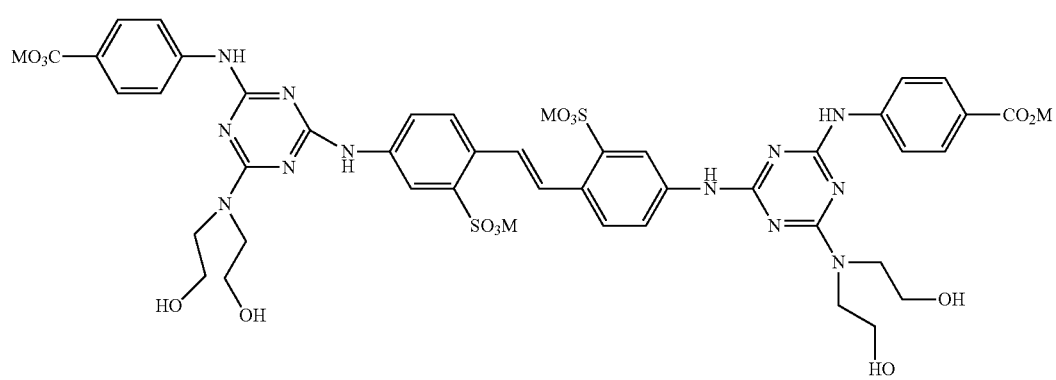

(1)

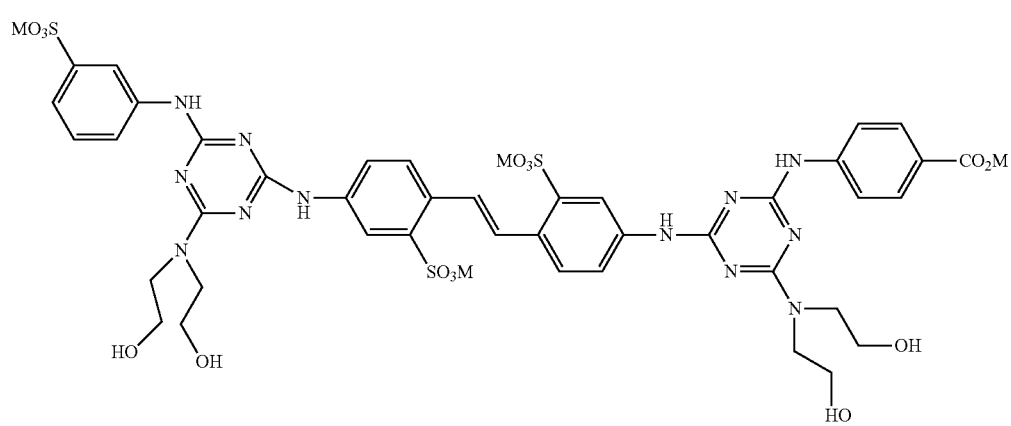

(2)

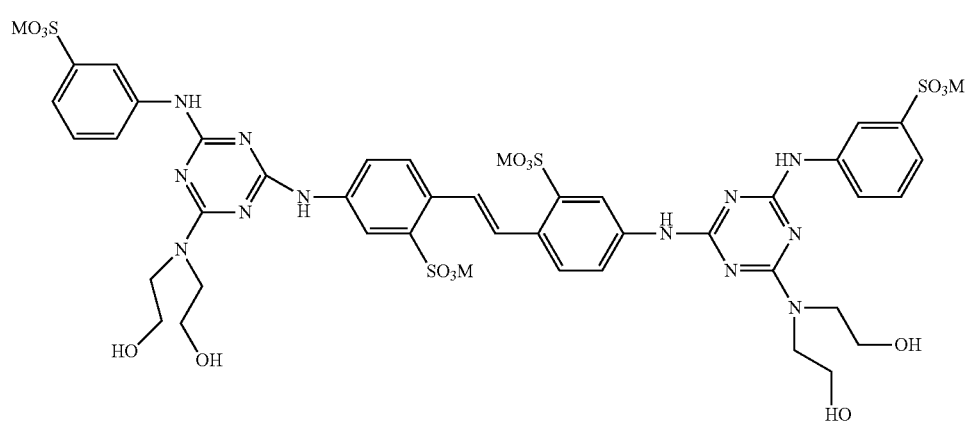

(3)

The amounts of the fluorescent whitening agents present in the composition depend on the number of fluorescent whitening agents present and which fluorescent whitening agents are present. According to the disclosure, the composition contains at least one fluorescent whitening agent of formula (1) in an amount of 0 to 99 weight-%, in other embodiments, 2 to 90 weight-%, and in still other embodiments 5 to 80 weight-%; at least one fluorescent whitening agent of formula (2) in an amount of 0 to 99 weight-%, in other embodiments 2 to 90 weight-%, and in still other embodiments 5 to 80 weight-%; and at least one fluorescent whitening agent of formula (3) in an amount of 0 to 99 weight-%, in other embodiments 2 to 90 weight-%, and in still other embodiments 5 to 80 weight-%; in each case based on 100 weight-% of the total amount of the present fluorescent whitening agents of the formulae (1), (2) and/or (3). In further embodiments, the composition contains at least one fluorescent whitening agent of formula (1) in an amount of 10 to 80 weight-%, in in other embodiments 20 to 70 weight-%, at least one fluorescent whitening agent of formula (2) in an amount of 10 to 60 weight-%, in other embodiments 10 to 50 weight-%, and at least one fluorescent whitening agent of formula (3) in an amount of 10 to 80 weight-%, in other embodiments 20 to 70 weight-%, in each case based on 100 weight-% of the total amount of the present fluorescent whitening agents of the formulae (1), (2) and/or (3).

The fluorescent whitening agent composition can be present in liquid form, in particular as a solution, or in form of a powder. In some embodiments, the compositions contain water in an amount of 20 to 90 weight-%, based on 100 weight-% of the total amount of the fluorescent whitening agents and water. Such aqueous fluorescent whitening agent compositions or mixtures are present in liquid form, in particular as a solution. Preferably, those are free of crystalline whitener particles such as their hydrate forms.

The fluorescent whitening agent compositions, in particular the aqueous compositions may contain a small amount of auxiliaries. This might be particularly relevant for fluorescent whitening agent compositions containing disulfo-type fluorescent whitening agents and/or if used in cold regions to enhance preparations' cold stability. In one embodiment, the aqueous fluorescent whitening agent composition contains less than 30% by weight, in other embodiments less than 20% by weight, and in still other embodiments less than 15% by weight, in yet other embodiments less than 10% by weight of components other than the fluorescent whitening agents and water. For example, formulation auxiliaries, such as standardizing agents, surface-active compositions, dispersants, antifoams, thickeners, preservatives, antifreezes, complexing agents, and/or electrolytes may be used. However, for ecological reasons, the aqueous fluorescent whitening agent preparation can contain very small amounts of other components, e.g. organic additives or auxiliaries, e.g., altogether less than 3% by weight, and in other embodiments less than 1% by weight, based on 100% by weight of the aqueous fluorescent whitening agent composition. In one embodiment, the composition contains no organic co-solvents, and/or urea. In another embodiment, the composition consists or consists essentially of the fluorescent whitening agents and water.

The aqueous fluorescent whitening agent composition can be prepared by introducing the fluorescent whitening agents of formulae (1), (2) and/or (3) or their mixture in the desired ratio in form of a powder or a concentrated solution thereof into water. Any auxiliaries can optionally be added during or after preparation of the mixture.

The disclosure further refers to the fluorescent whitening agent or compound of formula (2)

papermaking process used, the compositions can be added to the papermaking process also in diluted form, wherein the composition has been diluted to a desired concentration by addition of water and/or auxiliaries. In an embodiment, the aqueous, fluorescent whitening agent composition is introduced, optionally after dilution with water, to the pulp or pulp suspension. The compositions can be added continuously or discontinuously. The application is beneficial for both wood-containing pulps and wood-free pulps, in particular for wood-containing pulps. In surface application, the compositions can be used for preparing size press liquors, coating compositions or coating slips.

The aqueous fluorescent whitening agent compositions exhibit high storage stability and ease of application. Simultaneously, they provide high affinity (substantivity) to fibres and high whitening performance.

The disclosure also refers to a process for whitening paper, which comprises providing a pulp or pulp suspension; adding a fluorescent whitening agent composition as described above to the pulp or pulp suspension in an amount of 0.01 to 5% by weight in some embodiments, and 0.02 to 2% by weight in other embodiments, based on 100% by weight of dry pulp; producing a paper sheet from the pulp; and drying the sheet. In one embodiment of this process, the composition is added, after dilution with water and/or auxiliaries, in particular dilution with water, to the pulp or pulp suspension. In another embodiment of a process for whitening paper, a cellulose sheet is brought into contact with a fluorescent whitening agent composition as described above. The described processes for whitening paper also can be carried out by using the compound of formula (2).

The whiteness of the papers produced can be characterized by the CIE whiteness. Different fluorescent whitening agents can be compared to each other with respect to the saturation behaviour when determined according to CIE whiteness. In other words, if a larger amount of fluorescent whitening agent is used and no further increase in whiteness is found, there is

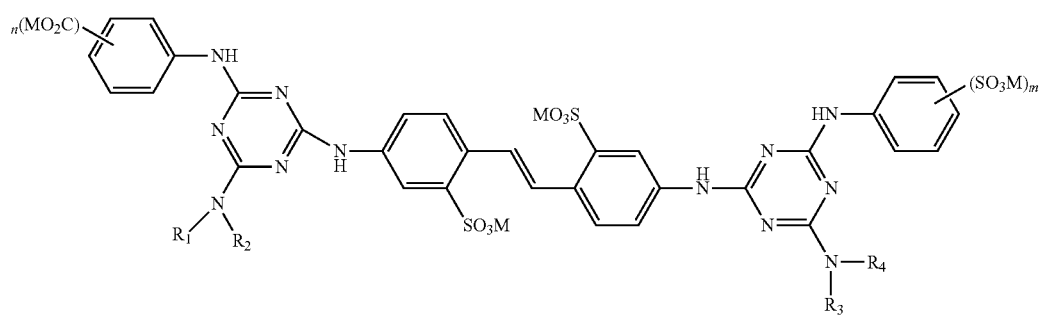

(2)

wherein n, m, M, $R_1$, $R_2$, $R_3$ and $R_4$ are as defined above. This compound is not known from the state of the art. It can be prepared by methods known in the art or as described above. Preferred embodiments for $R_1$, $R_2$, $R_3$, $R_4$, M, n and m are the same as described above for the composition according to the invention. The compound of formula (2) can be used as described below for the composition according to the disclosure.

The composition can be used for whitening paper or board, preferably in the pulp or pulp suspension (stock), in particular in the wet-end. Alternatively, the composition can be used for whitening paper at the surface. In wet-end applications, the compositions can be added at any point of the pulp circuit, e.g. chests or pipes, before sheet forming. Depending on the saturation behaviour and there may even be adverse effects on the whiteness when using higher amounts. The effect of saturation is also referred to as greening. The greening limit, i.e. the point at which increasing amounts of fluorescent whitening agent used results in virtually no further increase in whiteness, can be derived, for example, from the a*-b* diagram, where a* and b* are the colour coordinates in the CIE-L*a*b* system.

Paper produced by using the fluorescent whitening agent compositions according to the disclosure exhibits higher whiteness compared to paper produced using the typically used tetrasulfo-type fluorescent whitening agents. In particular it was found that when aminobenzoic acid (different isomers) is blended with aminosulfonic acid (different isomers)

in various ratios in the production process, the produced mixtures have better affinity to cellulose fibres than the corresponding tetrasulfo-type fluorescent whitening agents. Moreover, the performance of the obtained mixtures is superior to that of the corresponding tetrasulfo-type fluorescent whitening agents both in stock and surface applications, thus exhibiting an unexpected synergistic effect.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A composition suitable for optically whitening paper or board, comprising:
    at least two fluorescent whitening agents selected from the fluorescent whitening agents of formula (1), formula (2) and formula (3)

wherein n and m are, independently of each other, 0, 1, or 2, with the proviso that n and m are not both 0;
    $R_1$, $R_2$, $R_3$ and $R_4$ represent, independently of each other, hydrogen, cyano, $C_1$-$C_4$ alkyl, $C_2$-$C_4$ hydroxyalkyl, $C_2$-$C_4$ cyanoalkyl or $C_1$-$C_4$ alkoxyalkyl, or the residue of an amino acid from which a hydrogen atom has been abstracted from the amino group; or $R_1$ and $R_2$, or $R_3$ and $R_4$, independently of each other, together with N atom form morpholine, piperidine or pyrrolidine ring; or —$(CH_2)_l$—$SO_3M$, where l is 1, 2 or 3; or —$(CH_2)_i$—COOR, —$(CH_2)_i$—CONHR, —$(CH_2)_i$—COR, where i is an integer from 1 to 4, R is $C_1$-$C_3$ alkyl or has the same meaning as M;
    M represents hydrogen, or one equivalent of a cation, in particular Li, Na, K, Ca, Mg, ammonium, or ammonium which is mono-, di-, tri- or tetra-substituted by $C_1$-$C_4$ alkyl or $C_2$-$C_4$ hydroxyalkyl.

2. The composition of claim 1, wherein n and m are 1.

3. The composition of claim 1, wherein the groups —$CO_2M$ and —$SO_3M$ are, independently of each other, in an ortho- and/or apara-position.

4. The composition of claim 1, wherein $R_1$, $R_2$, $R_3$ and $R_4$ represent, independently of each other, a $C_2$-$C_4$ hydroxyalkyl, or a $C_1$-$C_4$ alkoxyalkyl.

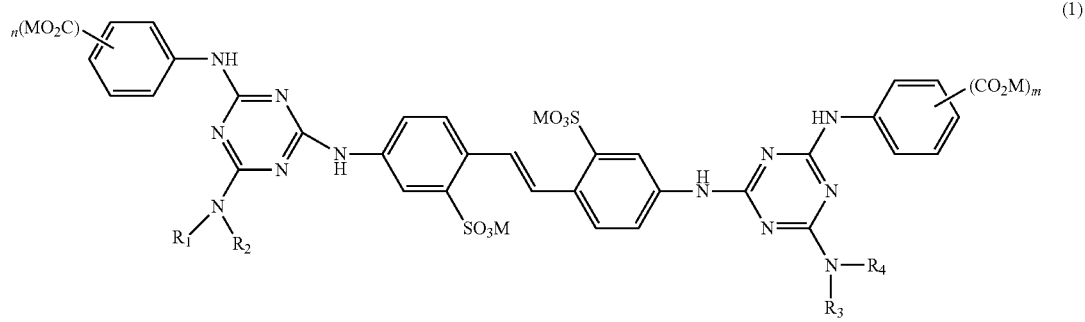

(1)

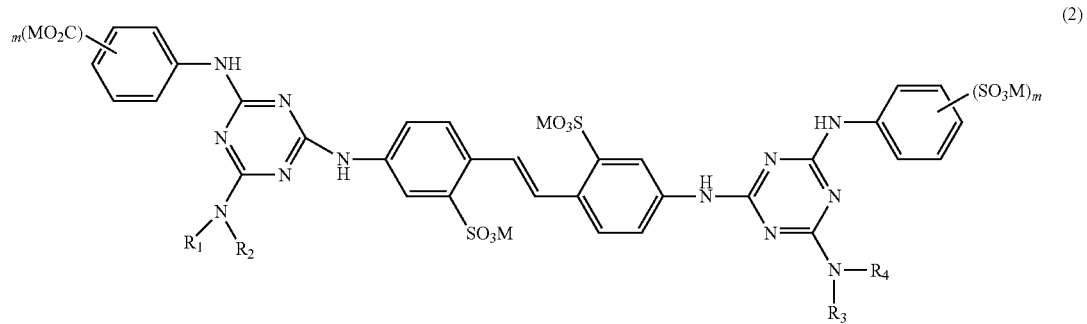

(2)

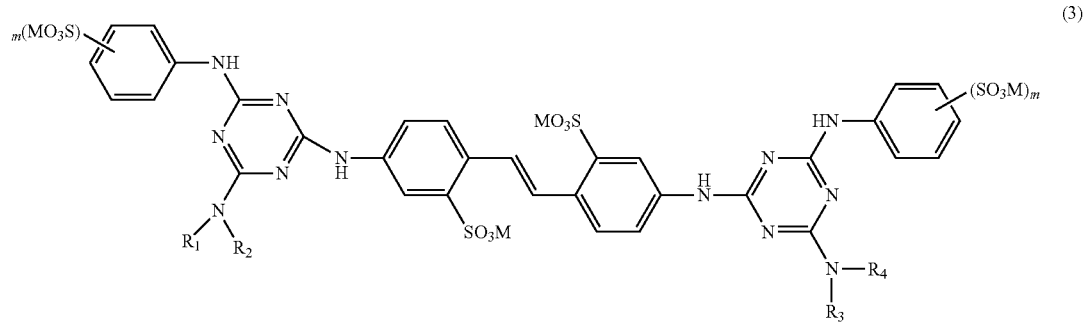

(3)

5. The composition of claim 1, wherein the composition contains a fluorescent whitening agent of the formula (2).

6. The composition of claim 5, wherein in the compound of the formula (2) n and m are 1, the group —$CO_2M$ is in ortho-position, and the group —$SO_3M$ is in para-position.

7. The composition of claim 1, wherein the composition contains the fluorescent whitening agents of formula (1), formula (2) and formula (3).

8. The composition of claim 1, wherein the composition contains the fluorescent whitening agent of formula (1) in an amount of 20 to 95 weight-%, the fluorescent whitening agent of formula (2) in an amount of 0.1 to 60 weight-%, and the fluorescent whitening agent of formula (3) in an amount of 0.1 to 30 weight-%, in each case based on 100 weight-% of the total amount of the fluorescent whitening agents of the formulae (1), (2) and/or (3).

9. The composition of claim 1, wherein the composition is an aqueous preparation.

10. The composition of claim 1, wherein the aqueous preparation is a size press liquor.

11. The composition of claim 1, wherein the aqueous preparation is a coating composition.

12. The composition of claim 1, wherein the aqueous preparation is a coating slip.

\* \* \* \* \*